(12) United States Patent
Synowicki et al.

(10) Patent No.: US 6,738,139 B1
(45) Date of Patent: May 18, 2004

(54) METHOD OF DETERMINING BULK REFRACTIVE INDICIES OF FLUIDS FROM THIN FILMS THEREOF

(75) Inventors: Ronald A. Synowicki, Lincoln, NE (US); Thomas E. Tiwald, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 0 days.

(21) Appl. No.: 10/407,578

(22) Filed: Apr. 7, 2003

Related U.S. Application Data

(60) Provisional application No. 60/405,845, filed on Aug. 26, 2002.

(51) Int. Cl.$^7$ .................................................. G01J 4/00

(52) U.S. Cl. ...................................................... 356/369

(58) Field of Search ................................. 356/369, 128, 356/134, 135, 630, 631, 632

(56) References Cited

U.S. PATENT DOCUMENTS

| | | | |
|---|---|---|---|
| 3,973,994 A | 8/1976 | Redfield | 136/89 |
| 3,985,447 A | 10/1976 | Aspnes | 356/118 |
| 4,514,582 A | 4/1985 | Tiedje et al. | 136/256 |
| 4,590,574 A | 5/1986 | Edmonds et al. | 364/498 |
| 4,683,160 A * | 7/1987 | Bloch et al. | 428/141 |
| 5,107,105 A | 4/1992 | Isobe | 250/225 |
| 5,420,680 A | 5/1995 | Isobe et al. | 365/128 |
| 5,502,560 A | 3/1996 | Anderson et al. | 356/128 |
| 5,610,708 A | 3/1997 | Anderson et al. | 356/128 |
| 5,910,842 A * | 6/1999 | Piwonka-Corle et al. | 356/369 |
| 6,392,756 B1 * | 5/2002 | Li et al. | 356/632 |
| 6,444,898 B1 * | 9/2002 | Fujisawa et al. | 136/256 |
| 2002/0003665 A1 * | 1/2002 | Mearini et al. | 359/586 |
| 2003/0025899 A1 * | 2/2003 | Amara et al. | 356/128 |

* cited by examiner

Primary Examiner—Michael P. Stafira
Assistant Examiner—Juan D Valentin, II
(74) Attorney, Agent, or Firm—James D. Welch

(57) ABSTRACT

Disclosed is a method for determination of bulk refractive indicies of fluids utilizing thin films thereof on a roughened surface of a two sided rigid or semi-rigid object.

8 Claims, 2 Drawing Sheets

METHOD OF DETERMINING BULK REFRACTIVE INDICIES OF FLUIDS FROM THIN FILMS THEREOF

The Application Claims Benefit from Provisional Application Ser. No. 60/405,845 Filed Aug. 26, 2002.

TECHNICAL FIELD

The disclosed invention relates to methodology for determination of bulk refractive indicies of fluids, and more specifically to determination of bulk refractive indicies of fluids utilizing thin films thereof on roughened surfaces.

BACKGROUND

It is known to determine the refractive indicies of bulk fluids utilizing Ellipsometry, Polarimetry, or Intensity techniques. Briefly, a beam of electromagnetism is caused to interact with a contained volume of said fluid and the resulting changes therein is monitored, said changes being related to the refractive index. Where Ellipsometry or Polarimetry are utilized, the electromagnetic beam is polarized.

A problem can develop where the volume of fluid is limited and the container for the fluid interacts with the fluid and effects or masks desired results. Further, where a bulk fluid is contained in an open surface container, said container must be maintained in an upright position and aligned with respect to the effect of gravity, to prevent fluid spillage therefrom.

The disclosed invention recognizes the identified problem and provides a solution in the form of providing a means for presenting a fluid which makes even very thin films thereof appear as optically think films.

A Search of patents was conducted with the disclosed invention in mind, the results of which follow.

While not obviating of the disclosed invention, probably the best prior art identified are U.S. Pat. Nos. 5,502,560 and 5,610,708 to Anderson et al., which describe apparatus comprising a diffraction grating, and methodology of its use in determining concentrations of materials in fluids. An element comprising a diffraction grating is placed into contact with a sample and a beam of polarized light is caused to pass through said element and reflect from the interface between said diffraction grating and the sample. The reflected spectrum is reported to have features related to the complex dielectric constant, which is dependent on concentrations of materials in the sample.

U.S. Pat. Nos. 5,307,105 and 5,420,680 to Isobe et al. describe apparatus and methodology for measuring refractive index and thickness of a thin film formed on a substrate.

U.S. Pat. No. 4,590,574 to Edmonds et al. describes a method for determining oxygen and carbon in a silicon substrate having a rough surface.

U.S. Pat. No. 4,514,582 to Tiedje et al. describes a system which enhances optical absorption in amorphous silicon comprising a substrate with a sandblasted surface, upon which is deposited a thin film of semiconductor.

U.S. Pat. No. 3,985,447 to Aspnes Is disclosed as it describes measurement of thickness and refractive index of a thin film on a substrate.

U.S. Pat. No. 3,973,994 to Redfield describes a solar cell comprising a thin layer of active semiconductor on the surface of a transparent substrate which has grooves present in the back side thereof.

Even in view of the prior art, need exists for a method which allows measurement of bulk refractive lndicies of a liquid using only a small amount thereof.

DISCLOSURE OF THE INVENTION

The disclosed invention is a method for measuring the bulk refractive index of fluids utilizing thin films thereof, and can be practiced with said thin film surface oriented facing either horizontally or vertically or at an in-between angle. Known procedures for alignment of solid samples can be utilized as a result of the provided simulated solid sample comprising a two sided, typically substantially flat rigid or semi-rigid object, one side thereof being roughened and having the fluid applied thereupon. Said surface roughening can be achieved by a variety of techniques, including common mechanical grinding or jet-spraying of abrasives onto a surface of a two sided, typically substantially flat rigid or semi-rigid object made of for instance, dielectric, (glass or polymer), metal, semiconductor or paper. Periodic re-wetting can become. necessary, however, where an absorbent material such as paper is utilized. Also, providing a quantity of fluid to said roughened side can be achieved by any functional approach-such as simple dripping thereonto, by spraying, painting or daubing. It is noted that low or high viscosity fluids, including gels, epoxies, photoresists and the like can be investigated utilizing the disclosed invention methodology, and that while fluids adhere to and conform to a roughened surface at the interface there between, an outer surface thereof is smooth and suitable for investigating by specular optical measurements using electromagnetic beams. Specular effects entered by the roughened surface have been found to be minimal. Further, even where fluids containing surfactants which eliminate tension adsorption effects, a thin film of fluid on said roughened surface of said two sided rigid or semi-rigid object can be oriented even vertically during investigation with an electromagnetic beam, as thin films of fluid adhere well to roughened surfaces and flow only extremely slowly.

The disclosed invention can be recited as a method of determining bulk refractive indices of fluids comprising providing a two sided, typically substantially flat rigid or semi-rigid object which has been roughened on at least one side thereof, and providing a quantity of fluid to said roughened side, followed by causing a source means of electromagnetic radiation to provide a beam of electromagnetic radiation and directing it to interact with said fluid coated substantially flat roughened surface of said two sided substantially flat rigid or semi-rigid object, such that it reflects from the thin film of said fluid and then enters a detector, such that the detector produces an output in response thereto. Performing an analysis of the detector output enables determination of bulk fluid refractive indicies.

The disclosed invention can alternatively be recitedas a method of determining bulk refractive indices of fluids comprising utilizing an ellipsometer system which comprises:

source means of electromagnetic radiation:

polarizer means;

sample supporting stage;

analyzer means;

detector means.

Said method comprises providing a two sided substantially flat rigid or semi-rigid object which has been roughened on at least one side thereof, and providing a quantity of fluid to said roughened side. It has been found that causing said ellipsometer system source means of electromagnetic radiation to provide a beam of electromagnetic radiation and directing it to pass through said polarizer, interact with said fluid coated substantially flat roughened surface of said two sided substantially flat rigid or semi-rigid object, such that it reflects from the thin film of said fluid, passes through said analyzer and then enters said detector, such that the detector produces an output in response thereto, enables performing an analysis of the detector output which enables determination of bulk fluid refractive indicies.

Benefits of the presently disclosed invention include elimination of ripples which result from external vibrations when volumes of fluid are subjected investigated, in addition to enabling easy alignment. In addition, as the fluid adheres well to the roughened surface, it can be held in place for extended periods of time, even where low viscosity fluids are investigated.

The disclosed invention can be practiced utilizing electromagnetic wavelengths in any range, including NIR, IR., Visual, UV etc., as long as the average roughness dimension is much greater than is the wavelength. Where this is the case a surface which appears rough at a given wavelength will also appear rough at nearby wavelengths. Reflections of electromagnetic radiation which enters the thin film and interacts with the roughened surface and make it to a detector have been found to be negligible, thereby making the thin film appear a infinitely thick. That this is the case is verified by measuring refractive indicies of both a thin film and a bulk volume of the same fluid, and obtaining the same result.

The disclosed invention can be practiced with any fluid which functionally adheres to a roughened surface, but is e particularly applicable to use with liquids.

The method can also involve the known practice of roughening the second side of the two sided substantially flat rigid or semi-rigid object to prevent backside reflections. This is typically necessary only where the refractive index of the roughened surface, in an important wavelength range, is very close to that of the fluid and electromagnetic radiation can reflect from said back surface and exit the fluid surface in a way that interferes with the electromagnetic radiation which reflect directly from said fluid surface.

The disclosed invention will be better understood by reference to the Detailed Description Section of this Specification in conjunction with reference to the Drawings.

SUMMARY OF THE INVENTION

It is therefore a purpose and/or objective of the disclosed invention to teach a method of utilizing small volume thin films of fluid to determine a bulk refractive index thereof.

Other purposes and/or objectives of the disclosed invention will become apparent by a reading of the Specification and Claims.

DETAILED DESCRIPTION

Figure 1:
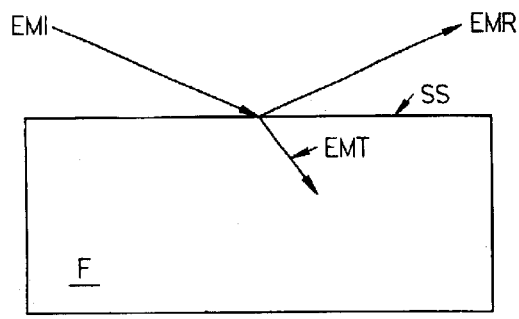
FIG. 1 demonstrates a prior art approach to determining bulk refractive indicies.

Turning now to the Drawings, FIG. 1 demonstrates a prior art approach to determining bulk refractive indicies. An incident electromagnetic beam (EMI) reflects from the smooth top surface (SS) of the effectively infinitely deep volume of fluid (F) as reflected electromagnetic beam (EMR). Any transmitted electromagnetic beam (EMT) can not reflect back out thereof as no functional backside of the fluid (P) is available to effect reflection. That is, the volume of fluid (F) provided is sufficient to be effectively infinitely deep.

Figure 2:
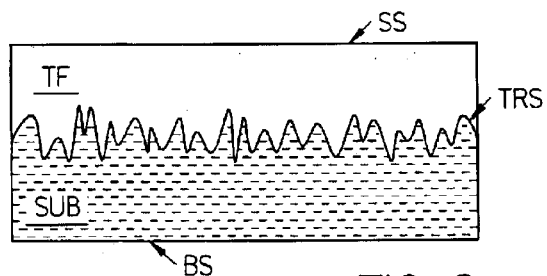
FIG. 2 shows a two sided substantially flat rigid or semi-rigid object, with a thin film of fluid on a roughened top side thereof.

FIG. 2 shows a disclosed invention two sided substantially flat rigid or semi-rigid object (SUB), with a smooth upper surfaced thin film (TF) of fluid present on-a-roughened top side (TRS) thereof.

Figure 3:
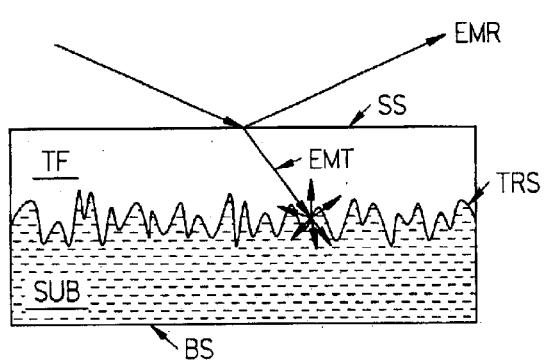
FIG. 3 demonstrates a disclosed invention approach to determining bulk refractive indicies, including indication of application of electromagnetic radiation thereto.

FIG. 3 demonstrates a disclosed invention approach to determining bulk refractive indicies utilizing only a thin film (TF) thereof, including indication of application of incident (EMI), and resulting smooth top surface (SS) reflected (EMR) and transmitted (EMT) electromagnetic radiation components. Note that transmitted (EMT) electromagnetic radiation is dispersed at the roughened top surface (TRS) and does not reflect in a way that interferes with the reflected (EMR) electromagnetic radiation.

Figure 4:
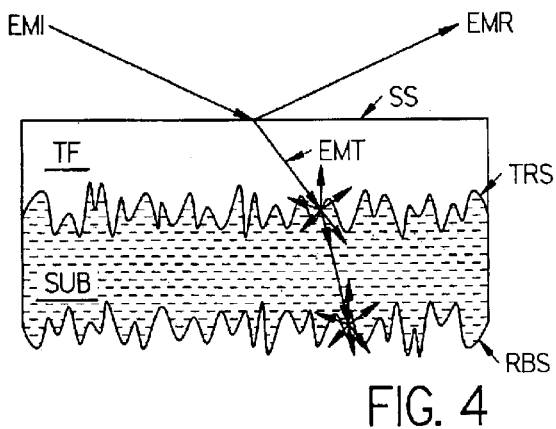
FIG. 4 demonstrates a disclosed invention approach to determining bulk refractive indicies wherein both sides of the two sided substantially flat rigid or semi-rigid object are roughened, including indication of application of electromagnetic radiation thereto.

FIG. 4 demonstrates a disclosed invention approach to determining bulk refractive indicies as in FIG. 3, but also shows the bottom side (RBS) of the two sided substantially flat rigid or semi-rigid object (SUB) is also roughened. Incident (EMI), and resulting top surface reflected (EMR) and transmitted (EMT) electromagnetic radiation components are again shown, along with dispersal of the transmitted electromagnetic beam where it interacts with the bottom roughened surface (RBS).

Figure 5:
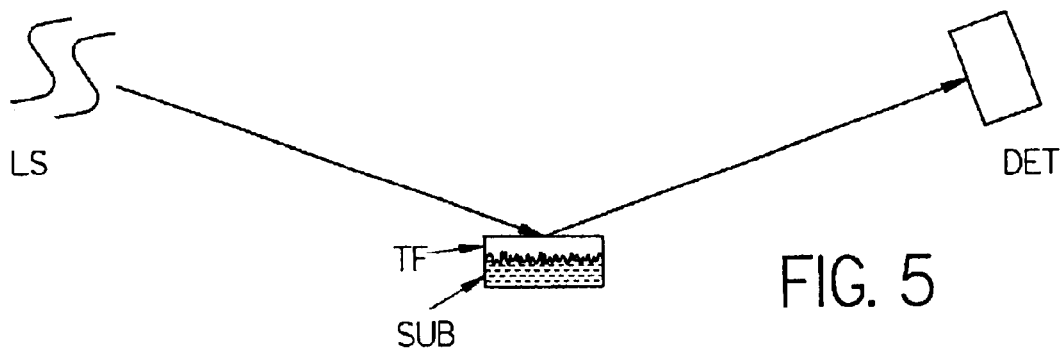
FIG. 5 shows an exemplary system for providing and detecting non-polarized electromagnetic radiation which is caused to interact with a two sided substantially flat rigid or semi-rigid object, at least the upper surface thereof being roughened.

FIG. 5 shows an exemplary system for providing and detecting non-polarized electromagnetic radiation which is caused to interact with a two sided substantially flat rigid or semi-rigid object (SUB), at least the upper surface thereof being roughened and to which is applied a thin film of fluid (TF). Shown are a source means (LS) of electromagnetic radiation, and a Detector (DET) and incident (EMI) and reflected (EMR) beams.

Figure 6:
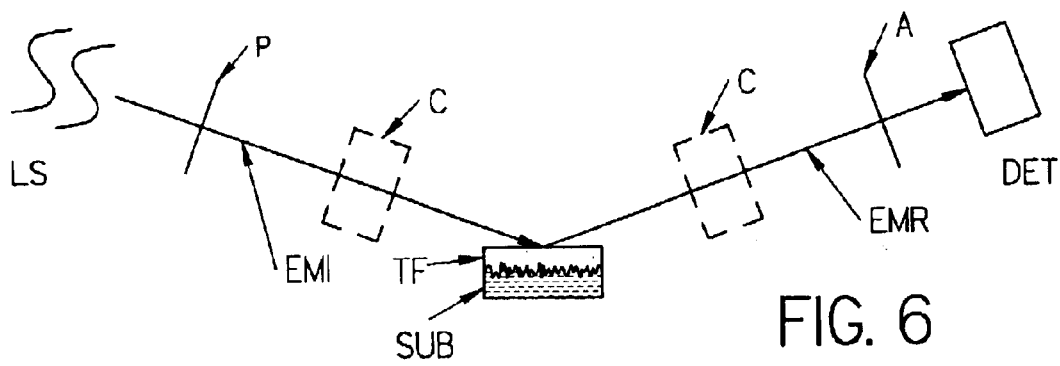
FIG. 6. shows an exemplary system for providing and detecting polarized electromagnetic radiation which is caused to interact with a two sided substantially flat rigid or semi-rigid object, at least the upper surface thereof being roughened.

FIG. 6 shows an exemplary system for providing and detecting polarized electromagnetic radiation which is caused to interact with a thin film of fluid (TF) present on a two sided substantially flat rigid or semi-rigid object (SUB) with a roughened upper surface. FIG. 6 is much as FIG. 5 but with added polarizer (P), analyzer (A) and optional compensators (C) (C').

Figure 7:
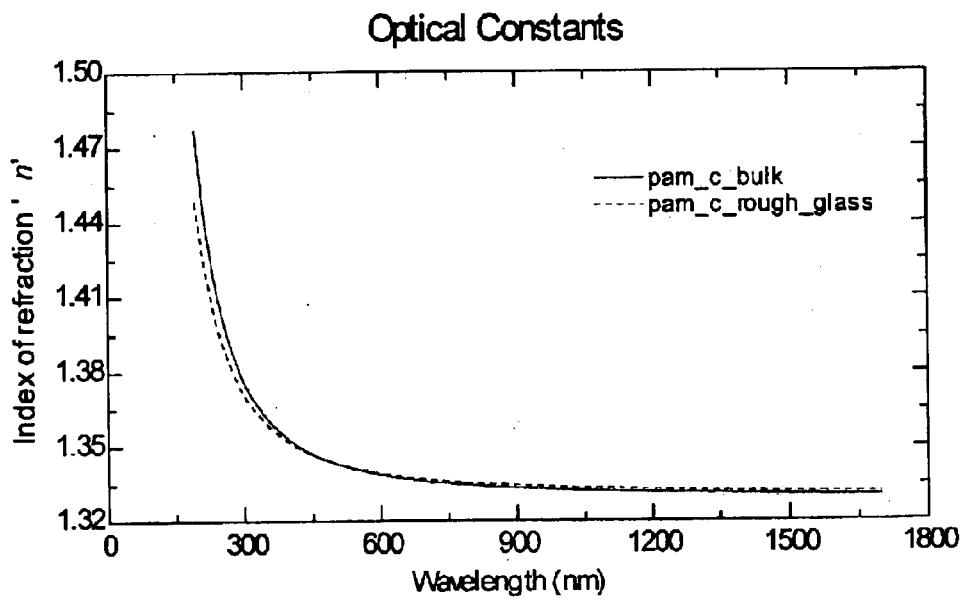
FIG. 7 demonstrates exemplary comparative experimental refractive index results determined both by conventional investigation of a bulk sample of PAM Cooking Surfactant, and by disclosed invention investigation of a thin film thereof.

FIG. 7 demonstrates exemplary comparative experimental refractive index results determined both by conventional investigation of a bulk sample of PAM Cooking Surfactant, and by disclosed invention investigation of a thin film thereof over a wide range, (ie 290–1700 nm), of wavelengths. Note the particularly good results between about 450–1700 nm. It is disclosed that a J.A. Woollam CO. M2000 (Registered Trademark), Spectroscopic Ellipsometer was used to obtain the data which when analyzed provided the results.

Note, the terminology "top" and "bottom" in the foregoing were utilized only to coordinate with the Drawings. A disclosed invention can be utilized with the two sided substantially flat rigid or semi-rigid object (SUB) in any orientation, such that the surface of the thin fluid (TF) faces in any direction.

Having hereby disclosed the subject matter of the present invention, it should be obvious that many modifications, substitution and variations of the present invention are possible in view of the teachings. It is therefore to be understood that the invention may be practiced other than as specifically described, and should be limited in its breadth and scope only by the Claims.

We claim:

1. A method of determining bulk refractive indices of liquids comprising the steps of:
   in any functional order practicing steps a, b and c:
   a) providing a quantity of liquid;
   b) providing a rigid or semi-rigid object comprising two sides which is roughened on first and second sides thereof;
   c) providing a source means of electromagnetic radiation, a sample supporting stage and detector means;
   d) covering the first roughened side of said rigid or semi-rigid object, with a thin film of said liquid;
   e) placing said rigid or semi-rigid object which has been covered with a thin film of said liquid on said first roughed side thereof, onto the sample supporting stage with said thin film of liquid being directly accessible;
   f) causing said source means of electromagnetic radiation to provide a beam of electromagnetic radiation and directing it to interact with and reflect from said thin film of liquid on said first roughened side of said rigid or semi-rigid object, and then enter said detector means such that it produces an output in response thereto;
   g) analyzing resulting detector means output to the end that bulk refractive indicies of the thin film of liquid are determined.

2. A method of determining the bulk refractive indices of liquids as in claim 1, in which the thin film of liquid on said first roughened side of said rigid or semi-rigid object is oriented to face in a direction selected from the group consisting of:
   vertically upward or downward;
   horizontally to the right or left; and
   in a direction between verical and horizontal.

3. A method of determining bulk refractive indices of liquids comprising the steps of:
   in any functional order practicing steps a, b and c:
   a) providing a quantity of liquid;
   b) providing a rigid or semi-rigid object comprising two sides which is roughened on first and second sides thereof;
   c) providing an ellipsometer or polarimeter system which comprises:
      source means of electromagnetic radiation:
      polarizer means;
      sample supporting stage;
      analyzer means;
      detector means;
   d) covering the first roughened side of said rigid or semi-rigid object, with a thin film of said liquid;
   e) placing said rigid or semi-rigid object which has been covered with a thin film of said liquid on said first roughed side thereof, onto the sample supporting stage of said ellipsometer system with said thin film of liquid being directly accessible;
   f) causing said ellipsometer or polarimeter system source means of electromagnetic radiation to provide a beam of electromagnetic radiation and directing it to pass through said polarizer, interact with and reflect from said thin film of liquid on said first roughened side of said rigid or semi-rigid object, pass through said analyzer and then enter said detector means such that it produces an output in response thereto;
   g) analyzing resulting detector means output to the end that bulk refractive indicies of the thin film of liquid are determined.

4. A method of determining the bulk refractive indices of liquids as in claim 3, in which the thin film of liquid on said first roughened side of said rigid or semi-rigid object is oriented to face in a direction selected from the group consisting of:
   vertically upward or downward;
   horizontally to the right or left; and
   in a direction between verical and horizontal.

5. A method of determining bulk refractive indices of fluids comprising the steps of:
   in any functional order practicing steps a, b and c:
   a) providing a quantity of fluid;
   b) providing a rigid or semi-rigid object comprising first and second sides which is roughened on both said first and second sides thereof;
   c) providing a source means of electromagnetic radiation, a sample supporting stage and detector means;
   d) covering said first roughened side of said rigid or semi-rigid object, with a thin film of said fluid;
   e) placing said rigid or semi-rigid object which has been covered with a thin film of said fluid on said first roughed side thereof, onto the sample supporting stage with said thin film of fluid being directly accessible;
   f) causing said source means of electromagnetic radiation to provide a beam of electromagnetic radiation and directing it to interact with and reflect from said thin film of fluid on said first roughened side of said rigid or semi-rigid object, and then enter said detector means such that it produces an output in response thereto;
   g) analyzing resulting detector means output to the end bulk refractive lndicies of the thin film of fluid are determined.

6. A method of determining the bulk refractive indices of fluids as in claim 5, in which the thin film of fluid on said first roughened side of said semi-rigid object is oriented to face in a direction selected from the group consisting of:
   vertically upward or downward;
   horizontally to the right or left; and
   in a direction between verical and horizontal.

7. A method of determining bulk refractive indices of fluids comprising the steps of:

in any functional order practicing steps a, b and c:
a) providing a quantity of fluid;
b) providing a rigid or semi-rigid object comprising two sides which is roughened on first and second sides thereof;
c) providing an ellipsometer or polarimeter system which comprises:
source means of electromagnetic radiation:
polarizer means;
sample supporting stage;
analyzer means;
detector means;
d) covering the first roughened side said rigid or semi-rigid object, with a thin film of said fluid;
e) placing said rigid or semi-rigid object which has been covered with a thin film of fluid on said first roughed side thereof, onto the sample supporting stage of said ellipsometer system with said thin film of fluid being directly accessible;
f) causing said ellipsometer or polarimeter system source means of electromagnetic radiation to provide a beam of electromagnetic radiation and directing it to pass through said polarizer, interact with and reflect from said thin film of fluid on said first roughened side of said rigid or semi-rigid object, pass through said analyzer and then enter said detector means such that it produces an output in response thereto;
g) analyzing resulting detector means output to the end that refractive indicies of the thin film of fluid are determined.

8. A method of determining the bulk refractive indices of fluids as in claim 7, in which the thin film of fluid on said first roughened side of said rigid or semi-rigid object is oriented to face in a direction selected from the group consisting of:

vertically upward or downward;

horizontally to the right or left; and in a direction between vertical and horizontal.

* * * * *